(12) United States Patent
Drummy

(10) Patent No.: US 8,138,755 B2
(45) Date of Patent: Mar. 20, 2012

(54) ENHANCED WIRELESS EDDY CURRENT PROBE FOR A NON-DESTRUCTIVE INSPECTION SYSTEM

(75) Inventor: Michael Drummy, North Reading, MA (US)

(73) Assignee: Olympus NDT, Waltham, MA (US)

( * ) Notice: Subject to any disclaimer, the term of this patent is extended or adjusted under 35 U.S.C. 154(b) by 284 days.

(21) Appl. No.: 12/500,767

(22) Filed: Jul. 10, 2009

(65) Prior Publication Data

US 2009/0273342 A1 Nov. 5, 2009

Related U.S. Application Data

(63) Continuation-in-part of application No. 12/425,976, filed on Apr. 17, 2009, now abandoned.

(60) Provisional application No. 61/046,011, filed on Apr. 18, 2008, provisional application No. 61/081,842, filed on Jul. 18, 2008.

(51) Int. Cl.
*G01N 27/82* (2006.01)

(52) U.S. Cl. ........ 324/240; 324/222; 324/228; 324/234; 324/236

(58) Field of Classification Search .................. None
See application file for complete search history.

(56) References Cited

U.S. PATENT DOCUMENTS

| | | | |
|---|---|---|---|
| 6,570,912 B1 * | 5/2003 | Mirfakhraei | 375/222 |
| 6,832,381 B1 * | 12/2004 | Mathur et al. | 719/328 |
| 2009/0243605 A1 * | 10/2009 | Bouregelas et al. | 324/242 |

* cited by examiner

*Primary Examiner* — Jermele M Hollington
*Assistant Examiner* — Trung Nguyen
(74) *Attorney, Agent, or Firm* — Ostrolenk Faber LLP

(57) ABSTRACT

An enhanced wireless eddy current probe is disclosed which has means to wirelessly couple to a non-destructive inspection (NDI) system situated some distance away from an inspection point on a material under inspection. The disclosed enhanced wireless eddy current probe provides means for executing advanced functions necessary for a complex eddy current inspection operation. These functions include, but are not limited to, storing, loading, and executing a predetermined firing sequence on an array of coil elements, probe balancing, probe calibration, and providing bibliographic information specific to said probe to a wirelessly coupled NDI system.

29 Claims, 6 Drawing Sheets

ENHANCED WIRELESS EDDY CURRENT PROBE FOR A NON-DESTRUCTIVE INSPECTION SYSTEM

CROSS REFERENCE TO RELATED APPLICATIONS

This application is a continuation-in-part of U.S. patent application Ser. No. 12/425,976 filed Apr. 17, 2009 entitled AN ENHANCED WIRELESS EDDY CURRENT PROBE FOR A NON-DESTRUCTIVE INSPECTION SYSTEM which claims the benefit and priority of U.S. Provisional patent application Ser. No. 61/046,011, filed Apr. 18, 2008, entitled AN ENHANCED WIRELESS EDDY CURRENT PROBE FOR USE WITHIN A NON-DESTRUCTIVE INSPECTION SYSTEM. This application also claims the benefit and priority of U.S. Provisional patent application Ser. No. 61/081,842, filed Jul. 18, 2008 entitled AN ENHANCED WIRELESS EDDY CURRENT PROBE FOR USE WITHIN A NON-DESTRUCTIVE INSPECTION SYSTEM, the entire disclosures of which are incorporated herein by reference.

BACKGROUND OF THE INVENTION

The present invention relates to non-destructive inspection (NDI) instruments, and more particularly to an enhanced wireless eddy current probe which provides advanced functionality including embedded diagnostics, power saving modes of operation, onboard status monitoring, embedded setup memory, means for coil element selection and interconnection, and wireless communication to a remote instrument.

Any discussion of the related art throughout this specification should in no way be considered as an admission that such art is widely known or forms a part of the common general knowledge in the field.

Eddy current inspection is a well known NDI technique used to examine conductive materials. In a typical eddy current inspection operation, an eddy current array probe, comprising a plurality of coils, is placed adjacent to the surface of a material under inspection. At the start of an inspection operation, an NDI instrument coupled to said eddy current array probe energizes one or more coils within the array. This, in turn, induces a current in the material under inspection. One or more coils within the probe array then sense this induced current and provide a measurement signal to the NDI instrument. By measuring the current induced in a material under inspection, the impedance of said material can be calculated. Further, by tracking the impedance of a material under inspection as the probe is moved along the surface of said material (or, in some NDI operations, comparing the measured impedance to that of a stored reference), flaws and defects within said material can be found and analyzed.

In a typical prior art eddy current NDI system, an eddy current probe is comprised of one or more coil elements which are coupled to an NDI instrument through a probe cable. Typically, at least two connections are made through the probe cable for each coil element within the probe. A first connection is made such that the NDI system to which a probe is coupled will have means to provide an excitation signal to each coil element within the probe. A second connection is made such that each coil element within the probe has means to provide a measurement signal sensed by that coil element to the NDI system for processing and analysis. In more complex systems wherein a single coil element will be excited or used to sense an induced current more than once within a firing sequence, more than two connections may be required to an individual coil element.

In many inspection systems, due to the plurality of connections required between the eddy current probe and the NDI system, the interconnecting probe cable becomes complex, expensive, and, in many cases, prone to damage. Moreover, in many NDI inspection operations one or more inspection points are located in difficult to access locations. Such locations include, but are not limited to, inspection points located a large distance away from the NDI system, inspection points which are located within hazardous locations wherein an inspection operator would be at personal risk during an inspection operation, or inspection points located within a complex structure, wherein said inspection points cannot be physically accessed without disassembly of said structure. Within such an inspection operation, the length of the interconnecting probe cable—often constrained by cost and signal integrity restrictions—can become a significant limitation for said operation.

U.S. Pat. No. 7,039,362 to Filkins et al. teaches an NDI system which uses a wireless transceiver between an NDI system and an ultrasonic inspection probe. While Filkins teaches a system which effectively overcomes the limitations of probe cable length, his solution is limited to and strictly addresses an ultrasonic system and is limited to an "uplink" path (a wireless communication path which provides means for signal transfer from an NDI system to an ultrasonic inspection probe) which transmits "timing pulse signals" to the ultrasonic probe and a "downlink" path (a wireless communication path which provides means for signal transfer from an ultrasonic inspection probe to an NDI system) which transmits only "envelope information" extracted from measurement data obtained by an ultrasonic inspection probe.

Filikins' wireless measurement probe interconnection system, while adequate for the specific ultrasonic NDI operation he describes, is insufficient to meet the needs of an eddy current NDI operation. Such NDI operations require excitation signals to be provided to individual coil elements and sensed measurement signals to be provided to the one or more receiver elements within the NDI system simultaneously during an inspection operation. Also, most eddy current inspection operations require that the full content of one or more measured signals (as opposed to simply the "envelope" information of said measured signals) be provided to the NDI system for proper analysis and processing. Further, within an inspection system comprising a multiple element eddy current array probe, the individual coils within the array probe are required to be excited and used to sense induced currents within an material under inspection in a predetermined sequence (commonly referred to as a firing sequence). Filkins' "timing pulse signals" do not provide a valid means to execute such a firing sequence within an eddy current NDI system.

A technical paper entitled "Wireless Eddy Current Probe for Health Engine Monitoring (Phase II)," published in "Review of Quantitative Nondestructive Evaluation Vol. 25" in 2006, and authored by Graubard et al. teaches a wireless NDI system specially designed for eddy current inspection. While Graubard's system provides sufficient means for transmitting measurement signals from a coil within an eddy current inspection probe to a remote, wirelessly couple NDI system, it does not provide means for said inspection probe to receive control signals from said NDI system. Further, Graubard's system fails to teach means for executing higher level inspection functions, which are commonly required in most eddy current NDI operations, via this wireless interface.

These higher level functions include, but are not limited to, executing a predetermined firing sequence on an eddy current array probe, balancing a probe prior to an inspection operation (that is, adjusting the measurement signal from each coil element such that said measurement signal will read zero in the impedance plane for a "good" measurement reading), and calibration of the measurement probe. Graubard also fails to provide a means for requesting from and communicating to an NDI system probe diagnostic and status information.

Accordingly, it would be advantageous to provide a wireless eddy current probe which has means to execute the advanced inspection functions required within common eddy current NDI operations. It would further be advantageous to provide a wireless eddy current probe which had means to provide diagnostic information to an NDI system to which it is wirelessly coupled.

SUMMARY OF THE DISCLOSURE

It is the object of the present disclosure to overcome the problems associated with prior art. This is attained by introducing the enhanced wireless eddy current probe of the present disclosure. In the preferred embodiment of the present disclosure, the enhanced wireless eddy current probe comprises a wireless transceiver element with means to both transmit and receive signals from a similar wireless transceiver element within to a non-destructive inspection (NDI) system, a microcontroller, a nonvolatile memory element, an excitation circuitry block, a multiplexer circuitry block, one or more coil elements, a receiver circuitry block, a signal processing block, a diagnostic circuitry block, a status indicator element, and a power supply. It should be noted that while the preferred embodiment of the present disclosure includes the totality of these elements, numerous alternate embodiments are also contemplated which contain a subset of these elements such as to optimize an enhanced wireless eddy current probe to a particular inspection operation.

The excitation circuitry block, the multiplexer circuitry block, the receiver circuitry block, and the signal processing block, responsive to control signals from the microcontroller, provide means to generate excitation signals, provide those excitation signals to individual coil elements as required by the predetermined firing sequence, simultaneously receive and process measurement signals sensed by individual coil elements as required by the predetermined firing sequence, and provide said measurements signals to the microcontroller. In the preferred embodiment of the present disclosure, the signal processing block comprises an analog to digital converter which digitizes the measurement signals sensed by the individual coil elements and provides these digitized representations to the microcontroller. In an alternate embodiment, this analog to digital converter is contained within the microcontroller itself. In another alternate embodiment of the present disclosure, the measurement signals sensed by the individual coil elements are not digitized within the enhanced wireless eddy current probe, but wirelessly transferred to an NDI system in analog form for signal processing and analysis.

The nonvolatile memory element is used to store probe specific information which can be accessed by the microcontroller during an inspection operation. Such information includes, but is not limited to, a data table describing a predetermined firing sequence to be executed during an inspection operation, previously stored balancing information, and bibliographic data, such as, but not limited to, a serial number, an installation date, or a probe's physical location within a structure under inspection.

The diagnostic circuitry block, responsive to control signals from the microcontroller, provides means for verifying the individual elements of the eddy current array probe and, in the preferred embodiment of the present disclosure, provides status information to the microcontroller and the status indicator element. The microcontroller then transmits this status information to the NDT system via the wireless transceiver element. In the preferred embodiment, the status indicator block also provides an indication of the functional status of the enhanced wireless eddy current probe of the present disclosure on the probe itself. The status indicator block comprises an external indicator mechanism, such as, but not limited to, LED indictor lights, an LCD display, or an audible alert tone on the probe housing which informs an operator working near the probe—but not necessarily near the NDI system wirelessly coupled to the probe—of the probe's diagnostic status.

A power supply is also provided within the enhanced wireless eddy current probe of the present disclosure such that the individual elements of the probe can be powered independently of the NDI system to which it is wirelessly coupled. In the preferred embodiment of the present disclosure, this power supply takes the form of a battery. In an alternate embodiment, however, electrical energy is provided to the power supply via an external power source, such as, but not limited to, a standard wall outlet or a power supply within the structure under inspection.

Accordingly it is the object of the present disclosure to provide an enhanced wireless eddy current probe which has means to execute advanced functions required for an eddy current inspection operation.

It is also an object of the present disclosure that these advanced functions include at least one of the following: executing a predetermined firing sequence, probe balancing, and probe calibration.

It is further an object of the present disclosure that this enhanced wireless eddy current probe have means to provide diagnostic information of the probe itself to a wirelessly coupled NDI system.

It is also an object of the present disclosure that the this enhanced wireless eddy current probe have means to provide diagnostic information to an operator, said means including, but not limited to, LED indicator lights, an LCD display, or an audible alert tone.

Other features and advantages of the present invention will become apparent from the following description of the invention that refers to the accompanying drawings.

DETAILED DESCRIPTION

Figure 1:
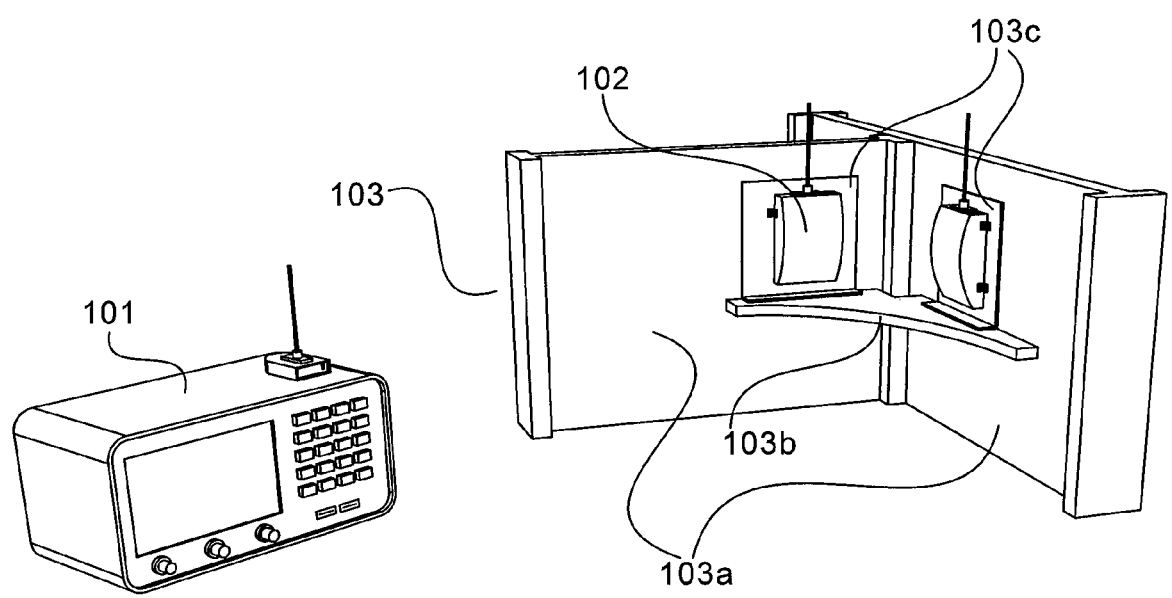
FIG. 1 is a perspective drawing of an exemplary non-destructive inspection operation which makes use of the enhanced wireless eddy current probe of the present disclosure.

FIG. 1 is a perspective drawing illustrating an exemplary non-destructive inspection (NDI) operation which makes use of the enhanced wireless eddy current probe of the present disclosure. An NDI system 101 is situated some distance away from a structure under inspection 103. Said structure 103 is comprised of a pair of support beams 103a, a bracing element 103b, and a pair of mounting brackets 103c. In this exemplary structure 103, said mounting brackets 103c are welded to the support beams 103a to hold bracing element 103b in place. In the exemplary NDI operation depicted in FIG. 1, the integrity of the welds fixing the mounting brackets 103c to the support beams 103a is the subject of the inspection. As such, an enhanced wireless eddy current probe 102 has been mounted over each weld point.

Figure 2:
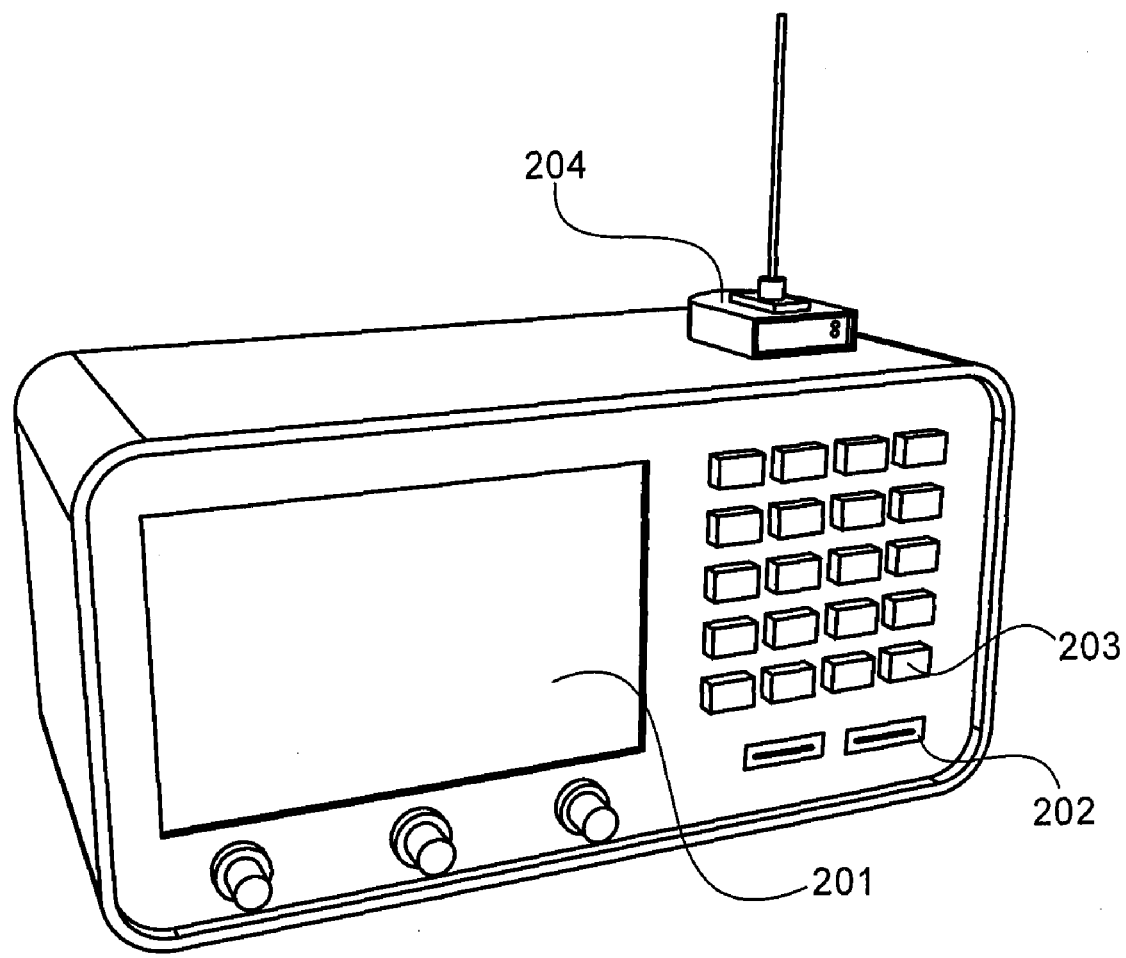
FIG. 2 is a close up perspective drawing of the non-destructive inspection system used in the inspection operation illustrated in FIG. 1.

FIG. 2 is a perspective drawing illustrating the NDI system used in the NDI operation depicted in FIG. 1. A functional block diagram of this NDI system is detailed in FIGS. 4A-4C. This exemplary NDI system comprises a display 201 and keypad 203, providing an operator interface, as well as a plurality of I/O ports 202, which provide means to download measurement data, upload operation specific setups, or update software. The design and structure of such an NDI system for use within an NDI eddy current inspection operation is well known to those skilled in the art.

A wireless transceiver 204 provides means for the NDI system to wirelessly couple to one or more remote enhanced wireless eddy current probes of the present disclosure. Many such transceiver elements are commercially available and their use and structure are well known to those skilled in the art. Similarly, a plurality of well established wireless data transfer protocols which make use of such wireless transceiver elements are well known to those skilled in the art. As such, the methods of the present disclosure should not be limited by the selection of wireless transceiver element or the specific method or protocol used to wirelessly couple the enhanced wireless eddy current probe to an NDI system.

Figure 3:
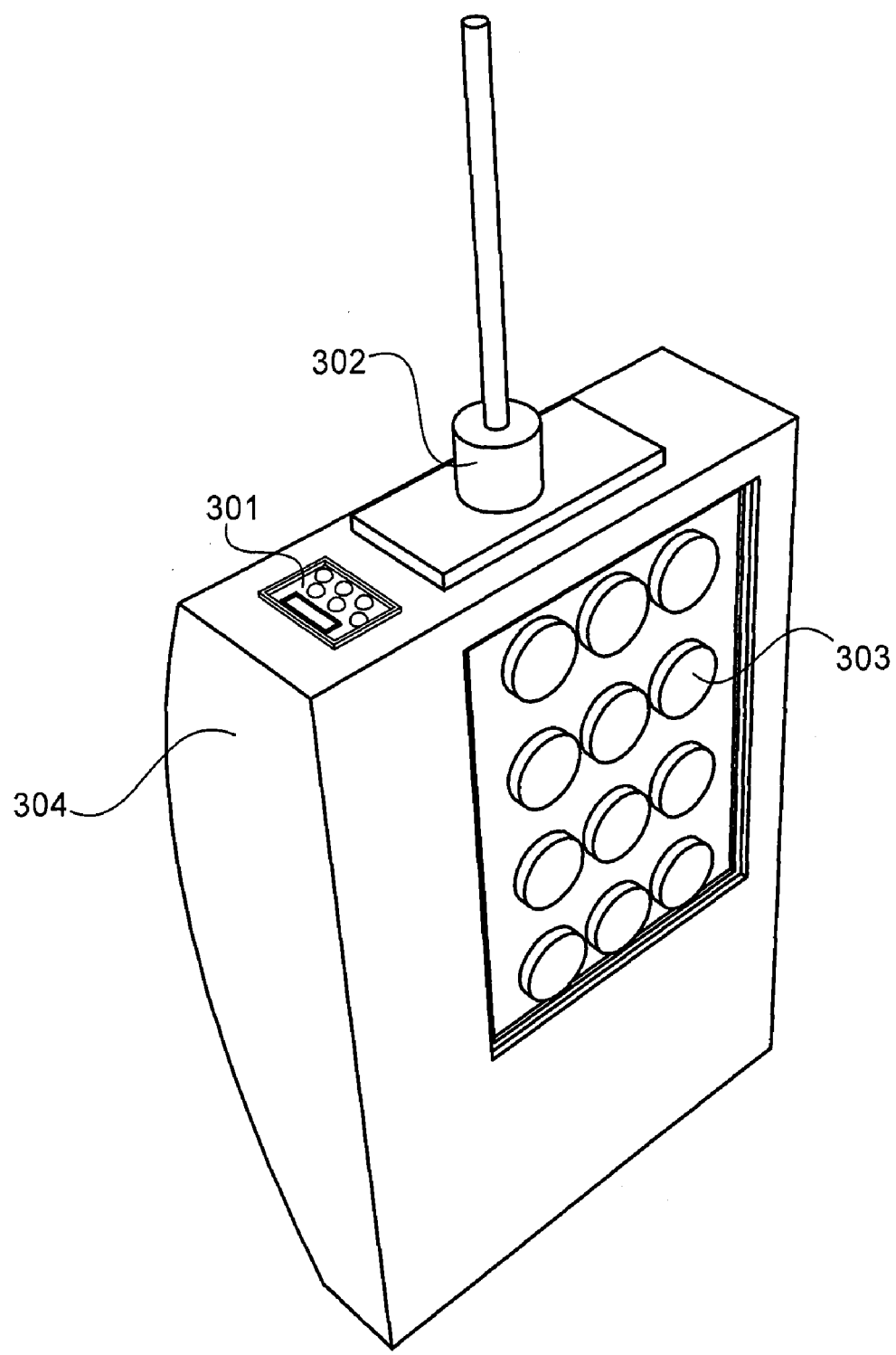
FIG. 3 is a close up perspective drawing of one of the enhanced wireless eddy current probes used in the inspection operation illustrated in FIG. 1.
Figure 4A:
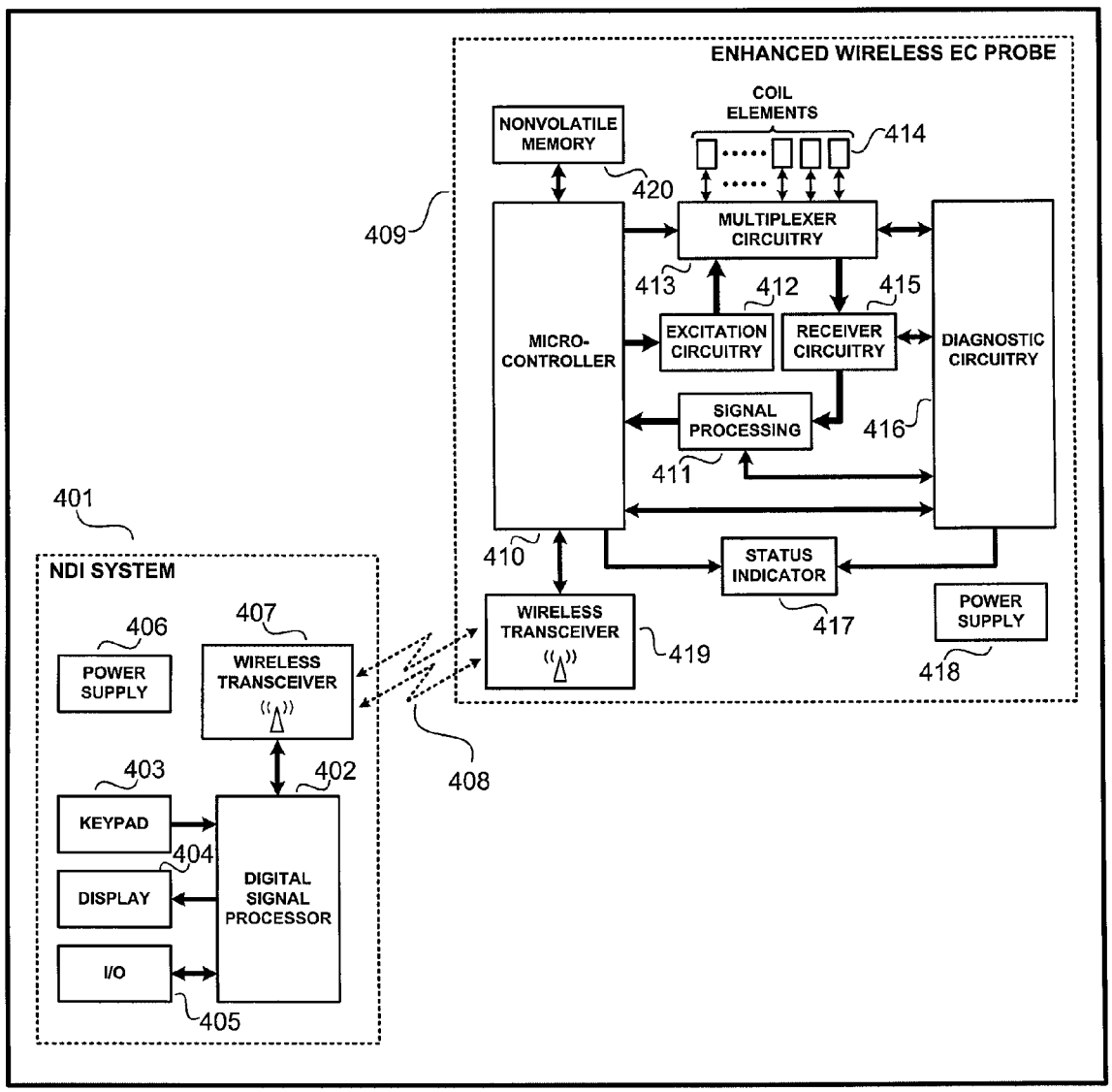
FIG. 4A is a block diagram of the preferred embodiment of the enhanced wireless eddy current probe of the present disclosure wherein said probe comprises an array of coils.
Figure 4B:
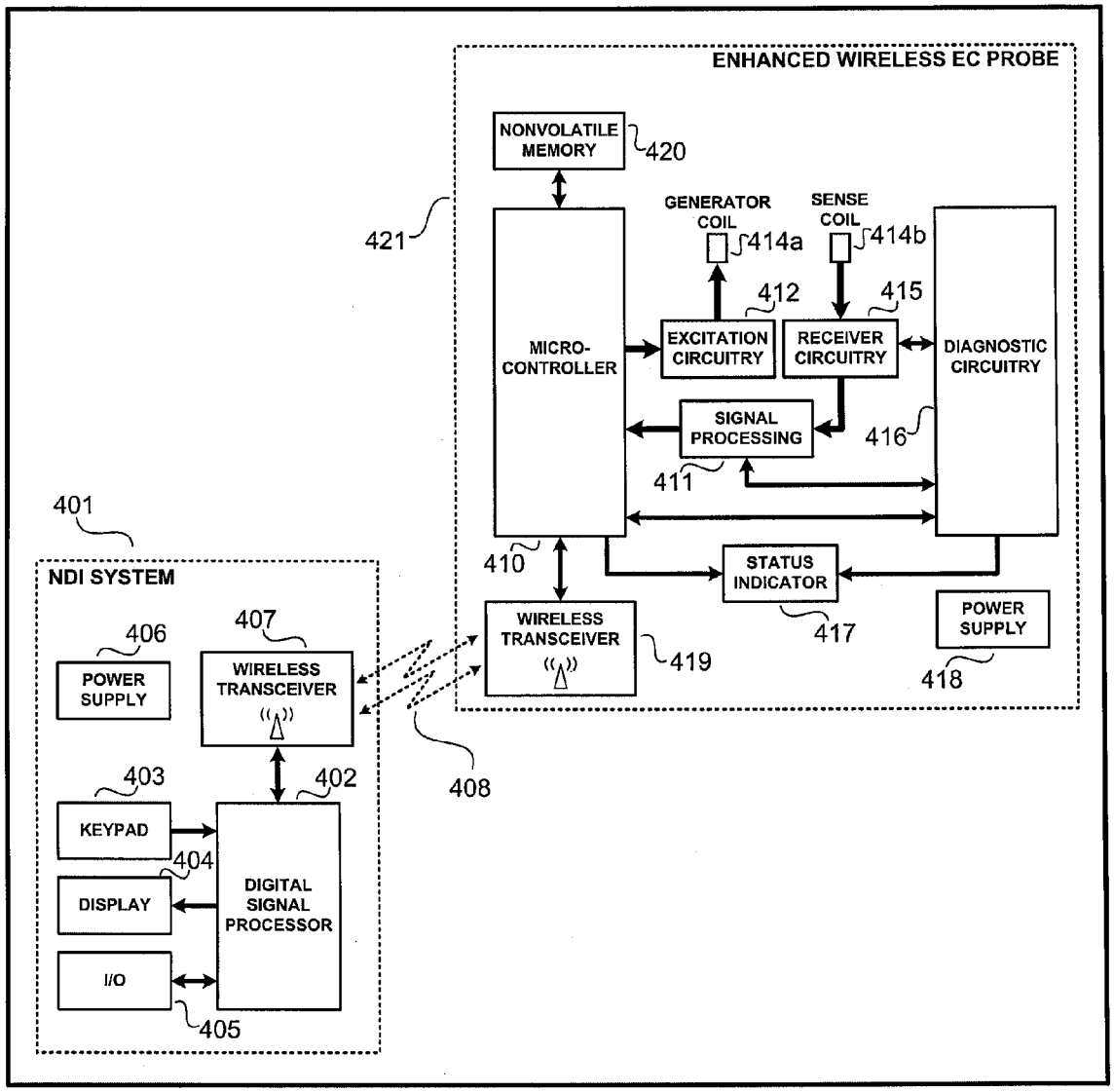
FIG. 4B is a block diagram of an alternate embodiment of the enhanced wireless eddy current probe of the present disclosure wherein said probe comprises one generator coil and one sense coil.
Figure 4C:
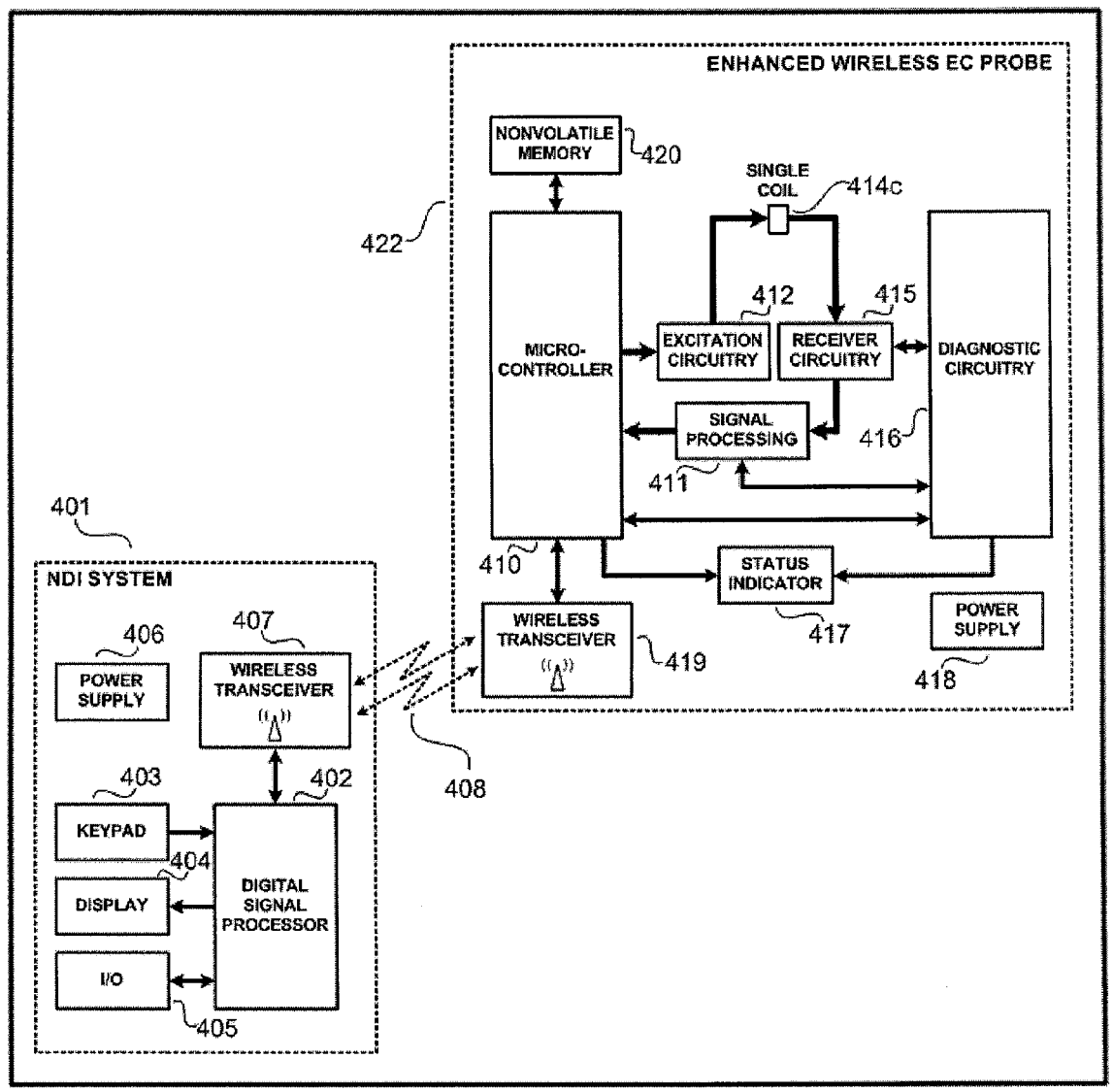
FIG. 4C is a block diagram of an alternate embodiment of the enhanced wireless eddy current probe of the present disclosure wherein said probe comprises a single coil.

FIG. 3 is a perspective drawing illustrating the enhanced wireless eddy current probe used in the exemplary inspection operation depicted in FIG. 1. A functional block diagram of the preferred embodiment of this probe is shown in FIG. 4A and discussed in detail in the explanation of that figure. Functional block diagrams further depicting alternate embodiments of this probe are shown in FIGS. 4B-4C and discussed in detail in the explanation of those figures. In the preferred embodiment of the present disclosure, this exemplary probe is comprised of an array of coil elements 303 which are placed adjacent to the area under inspection when the probe is mounted in place (refer to the placement of the enhanced wireless eddy current probe 102 in FIG. 1). A status indicator element 301 is fixed into the housing 304 of the enhanced wireless eddy current probe providing immediate diagnostic feedback to an operator physically inspecting the probe. It should be noted that this status indicator element 301 can be mounted on any location on the probe housing 304 as is convenient to a particular inspection operation. Finally, a wireless transceiver element 302 provides the probe means to wirelessly couple to the NDI system (101 in FIG. 1).

FIG. 4A is a functional block diagram illustrating the preferred embodiment of the enhanced wireless eddy current probe of the present disclosure 409 and an NDI system 401 to which it is wirelessly coupled. Within this embodiment, the enhanced wireless eddy current probe 409 is an array probe, comprising a plurality of coils. Looking first to the NDI system 401, a digital signal processor 402 is responsive to operator input via keypad element 403 and provides inspection data and other information to an operator through display element 404. An I/O interface 405 is provided to allow the digital signal processor 402 to provide measurement data to an external storage element, load inspection setups from an external system, have means to update the NDI system software, and the like.

It should be noted that while FIGS. 4A-4C depict a particular block diagram representation of an NDI System 401, such systems are well known to those skilled in the art. Further, it should be obvious to those skilled in the art that the NDI System 401 depicted in FIGS. 4A-4C could be replaced with a number of differing systems, including, but not limited to, systems including an FPGA element, systems including FLASH memory elements, or systems which include multiplexing units for interfacing with large eddy current array probes. Further the methods of the present disclosure are not limited by the specific design and makeup of the NDI system to which the enhanced wireless eddy current probe is coupled. As such, the specific NDI system 401 shown in FIGS. 4A-4C should be sufficient to represent the plurality of variations of such systems, which are well known to those skilled in the art.

Looking now to the enhanced wireless eddy current probe 409, a microcontroller 410 is coupled to wireless transceiver element 419, which is, in turn, wirelessly coupled to the wireless transceiver 407 within the NDI system 401. The digital signal processor 402 within the NDI system 401 communicates with the microcontroller 410 via the wireless communication path 408 established by the two wireless transceivers 407 and 419. Responsive to commands sent via the wireless communication path 408, the microcontroller has means to execute an inspection cycle, exciting coils elements 414 and acquiring measurement data. At the conclusion of such an inspection cycle, the microcontroller 410 can alternatively transmit said measurement data to the NDI system 401 via the wireless communication path 408 for processing and analysis or it can process that data itself and transmit back to the NDI system 401 some processed version of the data, including, but not limited to, a numerical measurement result which is ready for display to an operator.

For each step within a firing sequence (commonly referred to as time slots), one or more coil elements 414 are used as generator coils, and one or more coils are used as sense coils. The generator coils are provided with an excitation signal, which is generated within the excitation circuitry block 412, while the sense coils are coupled to the receiver circuitry block 415, such that measurements signals provided by these sense coils are provided to individual receiver elements within the receiver circuitry block 415. For each time slot, the receiver circuitry block 415 provides the one or more measurement signals provided by the individual coil elements 414 to the signal processing block 411 which, in turn, provides processed versions of said one or more measurement signals to the microcontroller 410.

In the preferred embodiment of the present disclosure the interconnections required for each time slot are executed by the multiplexer circuit block 413. Responsive to control signals from the microcontroller 410, the multiplexer circuitry block 413 interconnects individual coil elements 414 to both the excitation circuitry block 412 and the receiver circuitry block 415 as required by the predetermined firing sequence for each time slot. These control signals are generated within the microcontroller 410 according to a data table describing the predetermined firing sequence, this data table loaded into the microcontroller prior to the start of the inspection scan. Within this embodiment, the NDI system 401 need only transmit a single "start" signal over the wireless communication path 408 to execute a complete firing sequence scan. As such, the critically timed control and switching signals are generated and executed completely within the enhanced wireless eddy current probe 409, significantly simplifying the timing requirements of the control signals provided by the NDI system 401 via the wireless communication path 408.

In the preferred embodiment of the present disclosure, the data table describing the predetermined firing sequence is stored within the nonvolatile memory element 420. Prior to the start of an inspection scan, the microcontroller accesses this data table from within the nonvolatile memory element 420 and then uses said data table to generate the critically timed control signals provided to the multiplexer circuitry block 413. However, the methods of the present disclosure are not limited in this regard. In one alternate embodiment of the present disclosure, this firing sequence data is loaded into the microcontroller 410 from the NDI system 401 via the wireless communication path 408 prior to the start of the inspection operation. The microcontroller 410 can then execute this firing sequence by providing control signals to the multiplexer circuitry block 413. In another embodiment of the present disclosure, the interconnection control signals are provided to the enhanced wireless eddy current probe 409 via the wireless communication path 408 at each time slot. In this way, the critically timed control signals required to accurately execute the predetermined firing sequence are generated within and provided by the NDI system 401.

In the preferred embodiment of the present disclosure, the signal processing performed within the signal processing block 411 includes analog to digital conversion of the one or more measurement signals provided by the receiver circuitry block 415. In this way, digitized representations of the one or more measurement signals are provided to the microcontroller 410, which, in turn, provides the one or more digitized representations to the NDI system 401 via the wireless communication path 408 for further processing and analysis. In an alternate embodiment, the microcontroller 410 comprises one or more analog to digital converter elements which, responsive to processed analog measurement signals provided by the signal processing block 411, realize digitized representations of said analog measurement signals. As in the preferred embodiment, these digitized representations are then provided to the NDI system 401 via the wireless communication path 408 for further processing and analysis.

Alternatively, the individual coils of the probe 409 can be balanced prior to an inspection operation. This balancing operation can be initiated by a command sent via keypad 403 or retrieved from nonvolatile memory 420. Upon receiving the balancing command, the multiplexer circuit block 413 adjusts the measurement signal from each coil element such that the measurement signal all reads zero in the impedance plane.

Further alternatively, probe 409 can be calibrated prior to or during an inspection operation. This calibration operation can be initiated by a command sent via keypad 403, or retrieved from nonvolatile memory 420. Upon receipt of such calibration command via 419, Micro Controller 410 instructs any combination of the following three tasks to be performed.

1) Adjusting the phase angle or probe voltage of the probe 409 by adjusting the excitation circuitry 412.

2) Adjusting the probe's analog gain on the receiver circuitry 415.

3) Providing filtering at the receiver circuitry 415.

In another alternate embodiment of the present disclosure, the enhanced wireless eddy current probe 409 does not comprise means to digitize measurement signals sensed by individual coil elements 414. Within this embodiment, the processed analog measurement signals provided by the signal processing block 411 are transmitted to the NDI system 401 via the wireless communication path 408 in analog form.

The diagnostic circuitry block 416 provides means for monitoring the individual component elements of the enhanced wireless eddy current probe 409. In the preferred embodiment of the present disclosure, the diagnostic circuitry block 416, responsive to control signals provided by the microcontroller 410, has means to execute diagnostic tests on the plurality of elements which comprise the enhanced wireless eddy current probe 409. The results of said diagnostic tests are provided to the microcontroller 410, which, in turn, communicates the diagnostic status of the enhanced wireless eddy current probe 409 to the NDI system 401 via the wireless communication path 408. This diagnostic status includes, but is not limited to, diagnostic status of each of the individual probe elements, battery status, calibration parameters, and probe temperature. In the preferred embodiment of the present disclosure, the diagnostic circuitry block 416 also provides status signals to the status indicator block 417 such that the probe status indicator device (301 in FIG. 3) can provide feedback to an operator independent of the microcontroller 410. In the preferred embodiment of the present disclosure, the microcontroller 410 also provides control signals directly to the status indicator element 417 such that advanced diagnostics, which potentially require processing by the microcontroller 410, can be displayed on the probe status indicator device (301 in FIG. 4).

It should be noted that while the diagnostic circuitry block 416 has been shown as a separate, self-contained block within the functional block diagram shown in FIG. 4A for ease of explanation, the methods of the present disclosure are not limited in this regard. Indeed, in a practical electronic circuit system built according to the methods of the present disclosure, the diagnostic circuitry block 416 would most efficiently be realized with a plurality of circuit elements—responsive to control signals provided by the microcontroller 410—distributed among and built within the individual circuit elements built to realize the plurality of function blocks which comprise the enhanced wireless eddy current probe of the present disclosure. Further, the specifics of and details for creating and implementing such diagnostic circuitry within a system such as the enhanced wireless eddy current probe of the present disclosure are well known to those skilled in the art.

The nonvolatile memory element 420 can be used to store a variety of probe specific information necessary for a specific inspection operation for which the enhanced wireless eddy current probe of the present disclosure 409 has been selected. In the preferred embodiment of the present disclosure, this information can be accessed from the nonvolatile memory element 420 directly by microcontroller 410. The data stored with the nonvolatile memory element 420 can include, but is not limited to, one or more predetermined firing sequences optimized for one or more particular inspection operations, a previously acquired reference curve required to balance the individual coil elements 414 prior to an inspection scan, probe specific calibration parameters required for the individual coil elements 414, 414a, 414b, or 414c, and probe specific bibliographic data, including, but not limited to, a unique probe serial number, a model number, or an installation location. To this end, U.S. provisional patent application Ser. No. 60/971,293, which is included herein by reference, teaches the use of a nonvolatile memory element for storing balancing information within an eddy current array probe permanently coupled to a structure under inspection. Similarly, U.S. provisional patent application Ser. No. 61/039,471, which is included herein by reference, teaches the use of a nonvolatile memory element for storing firing sequence information within an eddy current probe.

The power supply element 418 is provided within the enhanced wireless eddy current probe of the present disclosure 409 such that the individual elements of the probe can be powered independently of the NDI system to which it is wirelessly coupled. In the preferred embodiment of the present disclosure, this power supply 418 takes the form of a battery. In an alternate embodiment, however, electrical energy is provided to the power supply via an external power source, such as, but not limited to, a standard wall outlet or a power supply within the structure under inspection. The microcontroller 410 has means to both provide and disengage energy from the power supply 418. In this way, responsive to controls from the NDI system 401, the microcontroller 410 can power down individual elements of the enhanced wireless eddy current probe when not in use, significantly reducing the requirements of the power supply 418.

FIG. 4B is a functional block diagram illustrating an alternate embodiment of the enhanced wireless eddy current probe of the present disclosure 421 and an NDI system 401 to which it is wirelessly coupled. It should be noted that the NDI system 401 shown in FIG. 4B is identical to that shown in and detailed in the discussion of FIG. 4A.

Within this embodiment, the enhanced wireless eddy current probe 421 is comprised of two coil elements, a first coil element 414a which is always used as a generator coil and a second coil element 414b which is always used as a sense coil. As such, the generator coil 414a is coupled directly to the excitation circuitry block 412, and the sense coil 414b is coupled directly to the receiver circuitry block 415. As this embodiment requires no interconnection sequence between multiple coil elements, no multiplexer circuitry block (413 in FIG. 4A) is necessary.

FIG. 4C is a functional block diagram illustrating another alternate embodiment of the enhanced wireless eddy current probe of the present disclosure 422 and an NDI system 401 to which it is wirelessly coupled. It should be noted that the NDI system 401 shown in FIG. 4C is identical to that shown in and detailed in the discussion of FIG. 4A.

Within this embodiment, the enhanced wireless eddy current probe 422 is comprised of a single coil element 414c, which is used both as a generator coil and as a sense coil. As such, the single coil element 414c is coupled directly to both the excitation circuitry block 412 and the receiver circuitry block 415. Since this embodiment requires no interconnection sequence between multiple coil elements, no multiplexer circuitry block (413 in FIG. 4A) is necessary.

In an alternate embodiment of the present disclosure, the coil elements (414 in FIG. 4A, 414a and 414b in FIG. 4B, and 414c in FIG. 4C) are contained within a housing separate from the main body of the enhanced wireless eddy current probe. This coil housing has means to couple with and decouple from the enhanced wireless eddy current probe such that a plurality of coil sets can be used with a single probe. In this way, the enhanced wireless eddy current probe of the present disclosure can used with a plurality of inspection operations.

It should be noted that the wireless communication described in the present disclosure can include the usage of many types of communication protocol to achieve signal communication among remote locations, including but not limited to many standard or private wireless protocols, the Internet protocol (TCPIP) and satellite communication protocols.

Although the present invention has been described in relation to particular embodiments thereof, many other variations and modifications and other uses will become apparent to those skilled in the art. It is preferred, therefore, that the present invention not be limited by the specific disclosure herein.

What is claimed is:

1. An eddy current, nondestructive inspection system to inspect a test object, comprising:
 a probe unit including a probe transceiver and located in a position to carry out tests of the test object;
 an NDI unit including an NDI transceiver and configured to operate the probe unit according to predetermined controlling commands including at least one excitation command via a remote communication path established between the probe transceiver and the NDI transceiver;
 the probe unit further comprising:
  at least one transducer element operable for inducing an eddy current in the test object according to the excitation command;
  a receiver circuit for receiving a signal from the test object in response to the eddy current; and
  a microcontroller for executing the controlling command and for transferring data from and to the NDI unit via the probe transceiver; and,
 the NDI unit further comprising:
  a signal processor configured to process the signal received from the probe unit; and
  a user interface.

2. The eddy current, nondestructive inspection system according to claim 1, wherein the probe unit further comprises a nonvolatile memory configured to store information enabling inspection operation of the probe unit.

3. The eddy current, nondestructive inspection system according to claim 1, wherein the at least one transducer element comprises a plurality of transducer elements.

4. The eddy current, nondestructive inspection system according to claim 3, wherein a first one of the plurality of transducer elements is a generator coil electrically connected to an excitation circuit, and a second one of the plurality of transducer elements is a sense coil electrically connected to the receiver circuit.

5. The eddy current, nondestructive inspection system according to claim 3, further comprising a multiplex circuit connecting the plurality of transducer elements to an excitation circuit and to the receiver circuit, the multiplex circuit configured to selectively excite or receive a signal from any of the transducer elements according to the control command.

6. The eddy current, nondestructive inspection system according to claim 3, wherein the plurality of transducer elements are arranged in an array.

7. The eddy current, nondestructive inspection system according to claim 3, further comprising a balancing facility configured to balance each of the transducer element prior to an inspection operation.

8. The eddy current, nondestructive inspection system according to claim 3, further comprising a calibration facility configured to calibrate each of the transducer element prior to an inspection operation.

9. The eddy current, nondestructive inspection system according to claim 1, wherein the probe unit comprises a status indicator for indicating a status of the probe unit.

10. The eddy current, nondestructive inspection system according to claim 9, wherein the status indicator is visible from an exterior of the probe unit.

11. The eddy current, nondestructive inspection system according to claim 1, wherein the NDI unit comprises one or more of a display, a user interface comprising a keypad, and at least one I/O data port.

12. An eddy current nondestructive inspection probe comprising:
at least one transducer element operable for inducing an eddy current in a test object according to at least one firing sequence command;
a receiver circuit for measuring a signal from the test object in response to the eddy current;
a probe transceiver configured for conducting communications remotely
with an NDI unit; wherein the NDI unit including an NDI transceiver, and a microcontroller for executing predetermined controlling commands from and sending the signal to the NDI unit via the probe transceiver and the NDI transceiver, wherein the controlling commands including the at least one firing sequence command for excitation of the eddy current.

13. The eddy current nondestructive inspection probe according to claim 12, wherein the probe unit further comprises a nonvolatile memory configured to store information enabling inspection operation of the probe unit.

14. An eddy current nondestructive inspection probe comprising:
at least one transducer element operable for inducing an eddy current in a test object
a receiver circuit for measuring a signal from the test object;
a probe transceiver configured for conducting communications remotely with an NDI unit; and
a microcontroller for executing predetermined controlling commands from and sending the signal to the NDI unit via the probe transceiver wherein the controlling commands including at least a firing sequence command for excitation of the eddy current,
wherein the at least one transducer element comprises a plurality of transducer elements.

15. The eddy current nondestructive inspection probe according to claim 14, wherein a first one of the plurality of transducer elements is a generator coil electrically connected to an excitation circuit, and a second one of the plurality of transducer elements is a sense coil electrically connected to the receiver circuit.

16. The eddy current nondestructive inspection probe according to claim 14, further comprising a multiplex circuit connecting the plurality of transducer elements to an excitation circuit and to the receiver circuit, the multiplex circuit configured to selectively excite or receive a signal from any of the transducer elements.

17. The eddy current nondestructive inspection probe according to claim 14, wherein the plurality of transducer elements are arranged in an array.

18. The eddy current nondestructive inspection probe according to claim 14, further comprising a balancing facility configured to balance each of the transducer elements prior to an inspection operation.

19. The eddy current, nondestructive inspection probe according to claim 14, further comprising a calibration facility configured to calibrate each of the transducer element prior to an inspection operation.

20. An eddy current nondestructive inspection probe comprising:
at least one transducer element operable for inducing an eddy current in a test object;
a receiver circuit for measuring a signal from the test object
a probe transceiver configured for conducting communications remotely with an NDI unit; and
a microcontroller for executing predetermined controlling commands from and sending the signal to the NDI unit via the probe transceiver, wherein the controlling commands including at least a firing sequence command for excitation of the eddy current,
wherein the probe further comprises a status indicator for indicating a status of the probe unit.

21. An eddy current, nondestructive inspection system to inspect a test object, comprising:
a probe unit including a probe transceiver and located in a position to carry out tests of the test object
an NDI unit including an NDI transceiver and configured to operate the probe unit according to predetermined controlling commands including at least one excitation command via a remote communication path established between the probe transceiver and the NDI transceiver;
the probe unit further comprising:
at least one transducer element operable for inducing an eddy current in the test object according to the excitation command;
a receiver circuit for receiving a signal from the test object in response to the eddy current; and
a microcontroller for executing the controlling command and for transferring data from and to the NDI unit via the probe transceiver; and,
the NDI unit further comprising:
a signal processor configured to process the signal received from the probe unit and
a user interface
further comprising a monitoring station, configured for communication with one or more of the probe unit and the NDI unit.

22. The eddy current, nondestructive inspection system according to claim 21, wherein the monitoring station comprises a memory for storing information received in communication with one or more of the probe unit and the NDI unit.

23. The eddy current, nondestructive inspection system according to claim 21, wherein the monitoring system is configured for wireless communication with one or more of the probe unit and the NDI unit.

24. The eddy current, nondestructive inspection system according to claim 21, wherein the monitoring system is configured to transmit messages to one or more of the probe unit and the NDI unit in response to predetermined criteria.

25. The eddy current, nondestructive inspection system according to claim 21, wherein the monitoring system is configured for communication with plural ones of the NDI unit and the probe unit.

26. The eddy current, nondestructive inspection system according to claim 1, wherein the probe unit is configured to read information from a machine-readable tag associated with the test object.

27. The eddy current, nondestructive inspection system according to claim 26, wherein the machine-readable tag comprises one or more of an RFID circuit, a bar code in one or more dimensions, and human-readable information.

28. The eddy current, nondestructive inspection system according to claim 1, wherein the probe unit further comprises a circuit operative to receive, decode and record positioning information relevant to signals of a Global Navigation Satellite System.

29. The eddy current, nondestructive inspection system according to claim 28, wherein the probe unit further comprises a circuit operative to report the positioning information to the NDI unit.

* * * * *